April 5, 1960 M. J. MURRAY Plant Pat. 1,927

MINT PLANT

Filed June 8, 1959

INVENTOR.
MERRITT J. MURRAY
BY Lindley E. Mills

United States Patent Office

Plant Pat. 1,927
Patented Apr. 5, 1960

1,927

MINT PLANT

Merritt J. Murray, Kalamazoo, Mich., assignor to A. M. Todd Company, Kalamazoo, Mich., a corporation of Michigan Application June 8, 1959, Serial No. 818,987

1 Claim. (Cl. 47—59)

Figure 1:
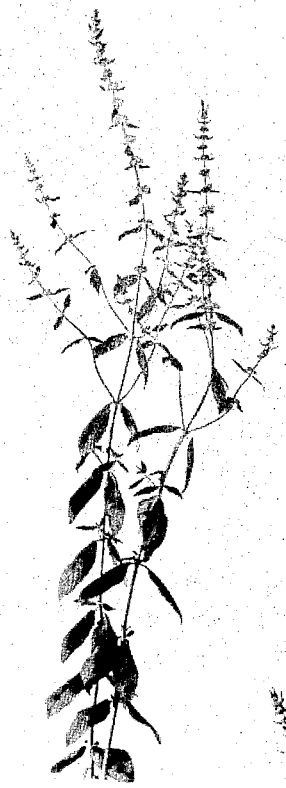

This invention relates to a new and distinct variety of mint plant which was initially produced by hybridization between *Mentha arvensis* L. var. *piperascens* Briq. and *Mentha crispa* L. (*Mentha spicata* L. var. *crispata*) and thereafter asexually reproduced from stolons at nurseries near Kalamazoo, Michigan. Although the variety of Plant Patent No. 1,614 and the variety of concurrently filed co-pending plant application Serial No. 818,986 resulted from the same cross, it will be apparent as the description proceeds that the variety described in this application is distinct from either of the other two varieties mentioned.

The new variety is characterized by its erect, medium-to-thickly branching habit and low growth, the plants generally growing to a height of somewhat less than three feet, often not more than slightly over two feet, under central Washington field conditions. The stems are sturdy and strong with numerous short branches near their upper ends, each of which generally develops into a flower spike. The new variety is hardy under southern Michigan and central Washington conditions. The colors of the plant and flowers are not distinctive and resemble those of the parent varieties when grown under comparable conditions.

The leaves of the new variety are somewhat broader in relation to their length than are the leaves of *Mentha arvensis* L. var. *piperascens* Briq. and are inclined to be decidedly oval at the base. The leaves are serrated similar to the leaves of *Mentha arvensis* L. var. *piperascens* Briq. but the serrations extend nearer to the base of the leaf. The leaves show little or no tendency to be wrinkled and curled as do the leaves of the varieties of Plant Patent No. 1,614 and of concurrently filed co-pending plant patent application Serial No. 818,986. The leaf stems and veins are medium hairy, the stems generally being more hairy than the veins.

The flowers are borne as axillary clusters on branched spikes, the clusters extending essentially to the base of the branch spikes in contrast to the flower-tipped branch spikes of the variety of co-pending plant patent application Serial No. 818,986. The leaves on the flower spikes are prominent and bract-like which, in the case of the lower flowers, often attain one-third their full size before the flowers open.

The new variety is not resistant to Verticillium wilt, *Verticillium alboatrum*, R. & B. var. *menthae* Nelson, or to spearmint rust, frequently identified as *Puccinia menthae* Pers., but is very highly resistant to powdery mildew, *Erysiphe cichoracearum* D.C. and to leaf spot diseases, including *Cephalosporium Sp.*, which attack *Mentha arvensis* L. var. *piperascens* Briq. Its resistance to attack by powdery mildew is particularly great, being greater than the resistance of either the variety of Plant Patent No. 1,614 or the variety of co-pending plant patent application Serial No. 818,986.

The resistance of the new variety to powdery mildew and leaf spot diseases was demonstrated in field plots on upland soil near Mentha, Michigan. Disease conditions were accentuated by interplantings of varieties and hybrids known to be susceptible to these diseases under the growing conditions employed and the infestation with powdery mildew was insured by scattering greenhouse grown plants of *Mentha arvensis* L. var. *piperascens* Briq. heavily infested with powdery mildew over the plots. The plots were continued for more than one year and additional new plots were planted adjacent to the undisturbed old plots each year during the test to insure a continuing inoculation of the new plots.

Susceptible varieties became heavily infested with mildew and leaf spot diseases in all plots whereas the new variety was infested to only an insignificant amount by these diseases. The greater resistance of the new variety to harmful infestation by powdery mildew as compared with the varieties of Plant Patent No. 1,614 and of co-pending plant patent application Serial No. 818,986 was particularly noticeable. Similar test procedures as regards powdery mildew and leaf spot diseases were carried out in central Washington under conditions of ditch irrigation with comparable results.

The new variety is particularly remarkable for the high total menthol content of its oil as compared with varieties resistant to attack by powdery mildew and leaf spot diseases which are suitable for field cultivation in central Washington and southern Michigan. This is all the more remarkable since one of the parents, *Mentha crispa* L., is a wild variety, the oil of which contains practically no menthol, and since the other parent, *Mentha arvensis* L. var. *piperascens* Briq., is known to be highly susceptible to these and many other diseases. The oil of the new variety usually contains from 81.5 to 87.3 percent total menthol as determined by the method for total menthol content given in the United States Pharmacopeia No. 14.

Figure 2:
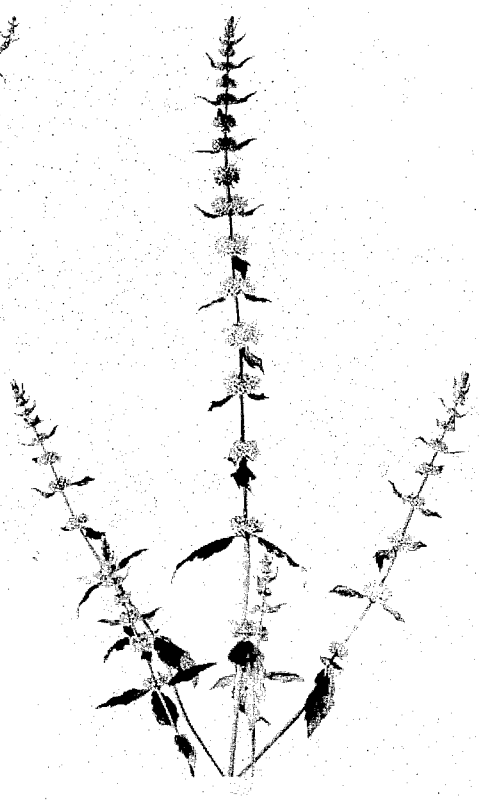

In the drawings, which are photographic illustrations of the new variety:

Figure 1 is a view of a pair of branches of the new variety showing the general form of the stems, leaves and flowers, and Figure 2 is an enlarged view of a flower stem illustrating the arrangement of the branch spikes, flowers and bract-like leaves.

The hybridization leading to the new variety was carried out in the summer of 1951 in southern Michigan. The seed resulting from the hybridization was planted and grown in the spring and summer of 1952. The new variety was selected from a large number of other hybrids as being of commercial value because of its erect habit and low growth, its very great resistance to powdery mildew, its high resistance to leaf spot diseases and for the high total menthol content of its oil as compared with other varieties sufficiently resistant to these diseases to be grown commercially in central Washington. The new variety was first asexually reproduced in the spring of 1953 in southern Michigan. It has been grown since 1953 by asexual reproduction from stolons, part of the time in central Washington, and part of the time in north central Oregon. It has consistently exhibited the foregoing characteristics since that time.

I claim:

A new and distinct variety of mint plant substantially as described, characterized particularly by its erect but low habit of growth, its high degree of resistance to powdery mildew, *Erysiphe cichoracearum* D.C. and leaf spot diseases, including *Cephalosporium sp.*, which attack *Mentha arvensis* L. var. *piperascens* Briq. and by the high menthol content of its oil as compared with other varieties resistant to these same diseases.

No references cited.